(12) United States Patent
Chen et al.

(10) Patent No.: US 11,832,645 B2
(45) Date of Patent: Dec. 5, 2023

(54) ELECTRONIC ATOMIZATION DEVICE AND ATOMIZER

(71) Applicant: SHENZHEN SMOORE TECHNOLOGY LIMITED, Shenzhen (CN)

(72) Inventors: Songkai Chen, Guangdong (CN); Jingjing Yang, Guangdong (CN); Jiyong Yang, Guangdong (CN); Guilin Lei, Guangdong (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 485 days.

(21) Appl. No.: 17/148,485

(22) Filed: Jan. 13, 2021

(65) Prior Publication Data

US 2021/0212375 A1    Jul. 15, 2021

(30) Foreign Application Priority Data

Jan. 15, 2020   (CN) .......................... 202010043355.4

(51) Int. Cl.
*A24F 40/48* (2020.01)
*A61M 15/00* (2006.01)
(Continued)

(52) U.S. Cl.
CPC ................ *A24F 40/48* (2020.01); *A24F 7/00* (2013.01); *A24F 40/10* (2020.01); *A24F 40/40* (2020.01);
(Continued)

(58) Field of Classification Search
CPC ........ A24F 40/10; A24F 40/48; A24F 40/485; A61M 15/0021
See application file for complete search history.

(56) References Cited

U.S. PATENT DOCUMENTS 30,828 A   12/1860   Mathers
1,001,225 A   8/1911   James
(Continued)

FOREIGN PATENT DOCUMENTS

CN   201042889 Y   4/2008
CN   100450790 C   1/2009
(Continued)

OTHER PUBLICATIONS

First office action of CN application No. 202010043355.4 dated Aug. 3, 2022.
(Continued)

*Primary Examiner* — Michael J Felton
*Assistant Examiner* — Ronnie Kirby Jordan
(74) *Attorney, Agent, or Firm* — Andrew C. Cheng

(57) ABSTRACT

The present disclosure relates to an electronic atomization device and an atomizer thereof. The atomizer includes a housing and an inhalation mouthpiece sleeved on an upper portion of the housing. A first air inlet channel communicating with the outside is provided between the inhalation mouthpiece and the housing. The housing is provided with a second air inlet port communicating with the first air inlet channel. The first air inlet channel is provided with a liquid absorption structure, which includes a plurality of first liquid absorption microgrooves provided on the outer sidewall portion of the housing that is located within the first air inlet channel. By providing the plurality of first liquid absorption microgrooves, most of the condensate can be absorbed by capillary tension and thus will not flow to the outside of the housing and the atomizer, thereby improving user experience and aesthetic appearance effect of the atomizer.

20 Claims, 9 Drawing Sheets

(51) Int. Cl.
    *A24F 40/10*     (2020.01)
    *A24F 7/00*     (2006.01)
    *A61M 15/06*     (2006.01)
    *A24F 40/40*     (2020.01)

(52) U.S. Cl.
    CPC ........ *A61M 15/0021* (2014.02); *A61M 15/06* (2013.01); *A61M 2205/8206* (2013.01)

(56) References Cited

U.S. PATENT DOCUMENTS

| | | | |
|---|---|---|---|
| 1,493,680 | A | 5/1924 | Koepsell |
| 2,427,243 | A | 9/1947 | Wahl |
| 2,431,015 | A | 11/1947 | Andrews et al. |
| 2,462,929 | A | 3/1949 | Zodtner |
| 2,522,553 | A | 9/1950 | Wittnebert |
| 2,522,554 | A | 9/1950 | Zodtner |
| 2,522,555 | A | 9/1950 | Bartell |
| 2,648,309 | A | 8/1953 | Bartell |
| 2,670,711 | A | 3/1954 | Wittnebert |
| 2,690,739 | A | 10/1954 | Weigel |
| 2,712,299 | A | 7/1955 | Rickmeyer |
| 2,724,366 | A | 11/1955 | Miessner |
| 2,782,763 | A | 2/1957 | Zodtner |
| 2,983,254 | A | 5/1961 | Silver |
| 3,116,719 | A | 1/1964 | Silver |
| 4,239,408 | A | 12/1980 | Mutschler |
| 2014/0261492 | A1 | 9/2014 | Kane et al. |
| 2016/0095354 | A1* | 4/2016 | Wu ................ A24F 47/008 |
| 2019/0116884 | A1 | 4/2019 | Conley et al. |

FOREIGN PATENT DOCUMENTS

| | | |
|---|---|---|
| CN | 201362062 Y | 12/2009 |
| CN | 201506120 U | 6/2010 |
| CN | 201580097 U | 9/2010 |
| CN | 203496486 U | 3/2014 |
| CN | 203952432 U | 11/2014 |
| CN | 203974294 U | 12/2014 |
| CN | 203974296 U | 12/2014 |
| CN | 203995225 U | 12/2014 |
| CN | 204180937 U | 3/2015 |
| CN | 101328312 B | 4/2015 |
| CN | 204414879 U | 6/2015 |
| CN | 105196735 A | 12/2015 |
| CN | 204845219 U | 12/2015 |
| CN | 204894859 U | 12/2015 |
| CN | 204936581 U | 1/2016 |
| CN | 205009816 U | 2/2016 |
| CN | 105415923 A | 3/2016 |
| CN | 103465683 B | 8/2016 |
| CN | 103465684 B | 8/2016 |
| CN | 105479977 B | 2/2017 |
| CN | 107284073 A | 10/2017 |
| CN | 206612365 U | 11/2017 |
| CN | 206841001 U | 1/2018 |
| CN | 107709034 A | 2/2018 |
| CN | 206978762 U | 2/2018 |
| CN | 105313536 B | 4/2018 |
| CN | 207449463 U | 6/2018 |
| CN | 106985572 B | 7/2018 |
| CN | 207594588 U | 7/2018 |
| CN | 207855281 U | 9/2018 |
| CN | 108725021 A | 11/2018 |
| CN | 109043676 A | 12/2018 |
| CN | 304968561 S | 12/2018 |
| CN | 109334302 A | 2/2019 |
| CN | 208630157 U | 3/2019 |
| CN | 110250576 A | 9/2019 |
| CN | 110613170 A | 12/2019 |
| CN | 110613171 A | 12/2019 |
| WO | 2018211390 A1 | 11/2018 |

OTHER PUBLICATIONS

First search report of CN application No. 202010043355.4 dated Aug. 3, 2022.
Extended European search report of EP application No. 21151342.9 dated Jun. 18, 2021.
The experimental study issued by China Academic Journal Electronic Publishing House.
The second office action with translation of CN application No. 202010043355.4 dated Apr. 29, 2023.

* cited by examiner

ELECTRONIC ATOMIZATION DEVICE AND ATOMIZER

FIELD

The present disclosure relates to atomization devices, and more particularly to an electronic atomization device and an atomizer thereof.

BACKGROUND

An electronic atomization device generally includes an atomizer for heating and atomizing aerosol generation substrate to generate an aerosol that may be inhaled by a user, and a power supply device for powering the atomizer. In the related art, during the use of the atomizer, a small part of aerosol vapour will usually enter an air inlet channel when the user inhales, and will partially condense when encountering sidewalls of the air inlet channel, forming condensate that may flow out from an air inlet. If not handled in time, the condensate would easily adhere to a housing of the atomizer, which may affect user experience and aesthetic appearance effect of the housing.

SUMMARY

The present disclosure is directed to an improved electronic atomization device and an atomizer thereof.

In one aspect, an atomizer is provided which include a housing and an inhalation mouthpiece sleeved on an upper portion of the housing. The inhalation mouthpiece and the housing define therebetween an air inlet channel communicating with an outside environment. The housing is provided with a second air inlet port communicating with the first air inlet channel. The first air inlet channel is provided with a liquid absorption structure, which includes a plurality of first liquid absorption microgrooves provided on an outer sidewall portion of the housing that is located within the first air inlet channel.

In some embodiments, each of the first liquid absorption microgrooves is arranged to extend along a circumferential direction of the housing.

In some embodiments, the first liquid absorption microgroove has a groove width of 0.05-1 mm.

In some embodiments, at least one air inlet groove is formed on the outer sidewall portion of the housing that located within the first air inlet channel, and the air inlet groove communicates with the first air inlet channel and the second air inlet port.

In some embodiments, the at least one air inlet groove traverses the first liquid absorption microgroove.

In some embodiments, the air inlet groove is arranged to extend along a longitudinal direction of the housing.

In some embodiments, the air inlet groove is arranged in a bent or spiral form.

In some embodiments, a first air inlet port communicating with the first air inlet channel is provided between an open end portion of the inhalation mouthpiece and the housing, and the air inlet groove is communicating with the first air inlet port.

In some embodiments, an atomization cavity is formed inside the housing. A second air inlet channel and a first air outlet channel that communicate with the atomization cavity are formed inside the housing, and the second air inlet channel communicates with the second air inlet port.

In some embodiments, at least one of the plurality of first liquid absorption microgrooves communicates with the first air outlet channel.

In some embodiments, a liquid guiding groove communicating the first liquid absorption microgroove with the first air outlet channel is formed on the outer sidewall of the upper portion of the housing.

In some embodiments, the atomizer further includes an atomization seat arranged in the housing and an atomization assembly arranged in the atomization seat. The atomization cavity is formed inside the atomization seat. The atomization seat is provided with a third air inlet channel communicating with the second air inlet channel and the atomization cavity, an activation air channel communicating with the second air inlet channel, and a second air outlet channel communicating with the atomization cavity and the first air outlet channel.

In some embodiments, the activation air channel and the third air inlet channel are arranged side by side and in parallel.

In another aspect, an electronic atomization device is provided which includes a power supply device and an atomizer connected to the power supply device. The atomizer includes a housing and an inhalation mouthpiece sleeved on an upper portion of the housing. The inhalation mouthpiece and the housing define therebetween a first air inlet channel communicating with an outside environment. The housing is provided with a second air inlet port communicating with the first air inlet channel. The first air inlet channel is provided with a liquid absorption structure, which includes a plurality of first liquid absorption microgrooves provided on an outer sidewall portion of the housing that is located within the first air inlet channel.

In various embodiments of the present disclosure, the atomizer is provided with the liquid absorption structure in the first air inlet channel, specifically, the outer sidewall portion of the housing located within the first air inlet channel is provided with the plurality of first liquid absorption microgrooves, such that most of the condensate can be absorbed by capillary tension and thus will not flow to the outer surface of the housing and the outside of the atomizer, thereby improving the user experience and the aesthetic appearance effect of the atomizer.

BRIEF DESCRIPTION OF THE DRAWINGS

The present disclosure will be further described below in conjunction with the accompanying drawings and embodiments, in which.

DESCRIPTION OF THE EMBODIMENTS

In order to provide a better understanding of the technical features, objectives and effects of the present disclosure, particular embodiments of the present disclosure will now be described in detail with reference to the accompanying drawings.

It should be understood that the terms "front", "rear", "left", "right", "upper", "lower", "first", "second" and the like are used only for the convenience of describing the technical solutions of the present disclosure, rather than indicating that the referred device or element must have special differences, and thus they should not be understood as limitations of the present disclosure. It should be noted that when one element is considered to be "connected to" another element, it may be directly connected to the other element or may be indirectly connected to the other element, i.e., an intervening element may be present. Unless otherwise defined, all technical and scientific terms used herein have the same meaning as commonly understood by those skilled in the technical field of the present disclosure. The terms used in the description of the present disclosure herein are only for the purpose of describing specific embodiments, and are not intended to limit the present disclosure.

Figure 1:
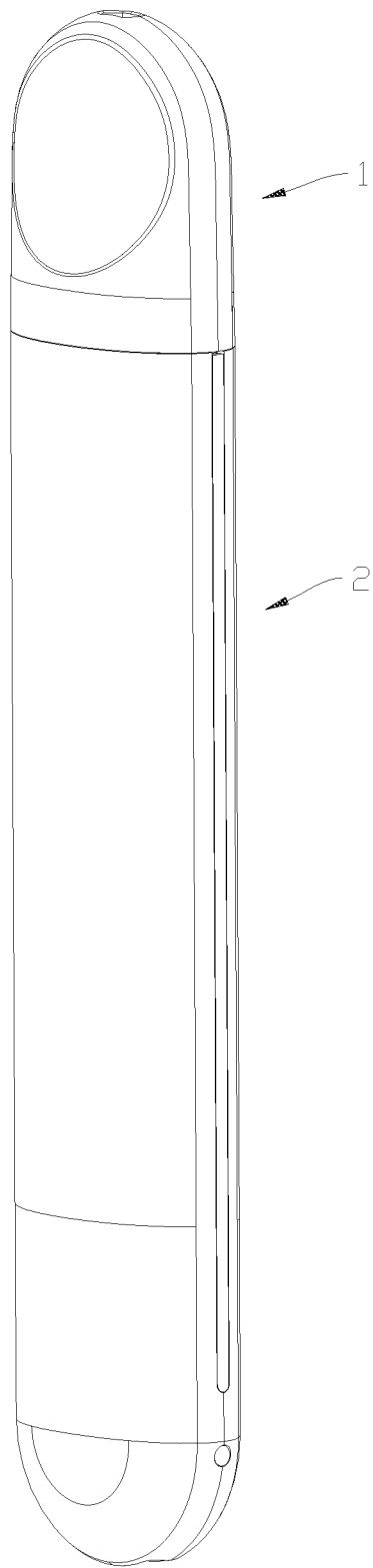
FIG. 1 is a schematic perspective view of an electronic atomization device according to some embodiments of the present disclosure.
Figure 2:
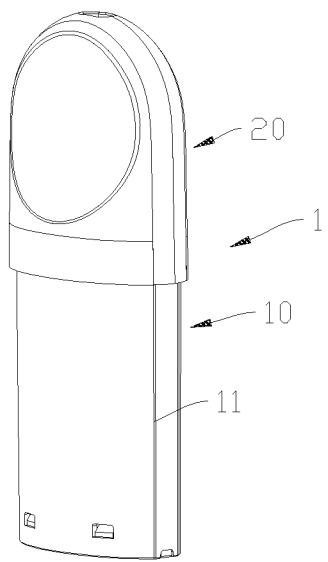
FIG. 2 is a partially exploded schematic view of the electronic atomization device shown in FIG. 1.
Figure 2:
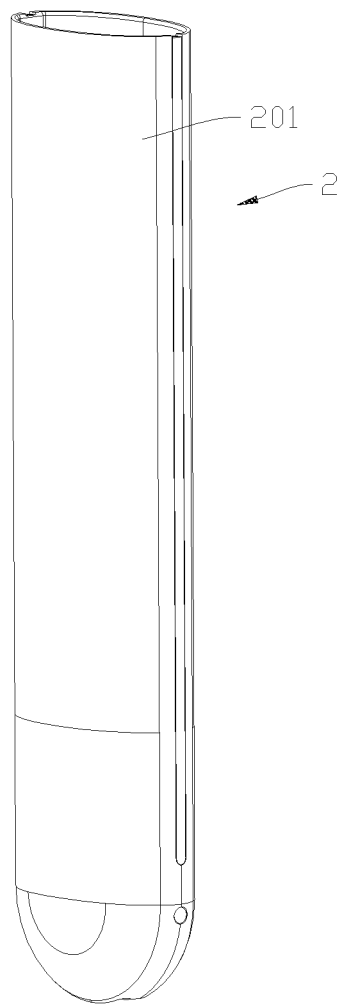
Figure 3:
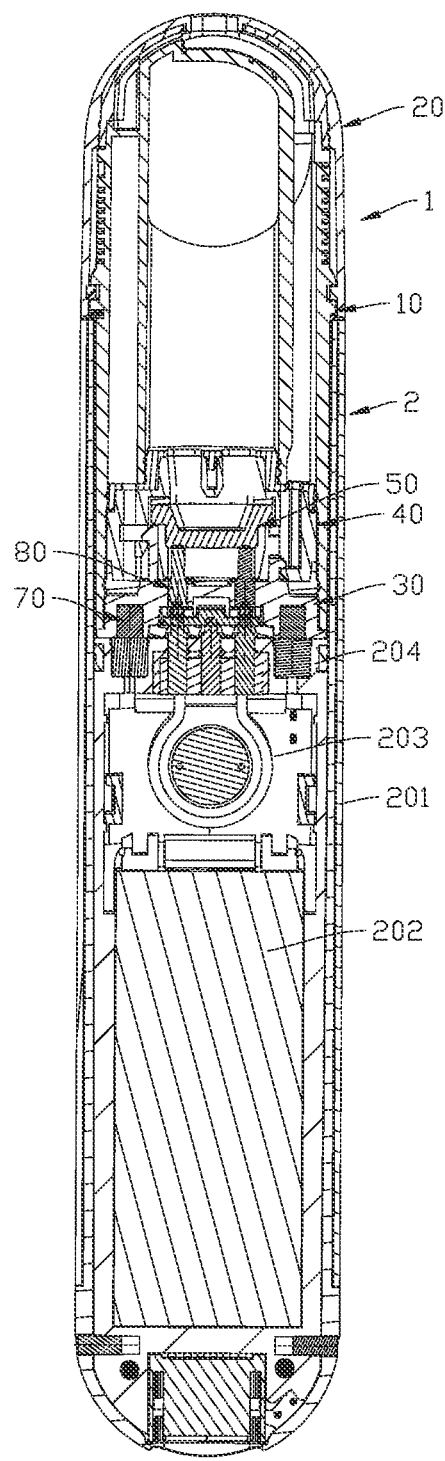
FIG. 3 is a cross-sectional view of the electronic atomization device shown in FIG. 1.
Figure 4:
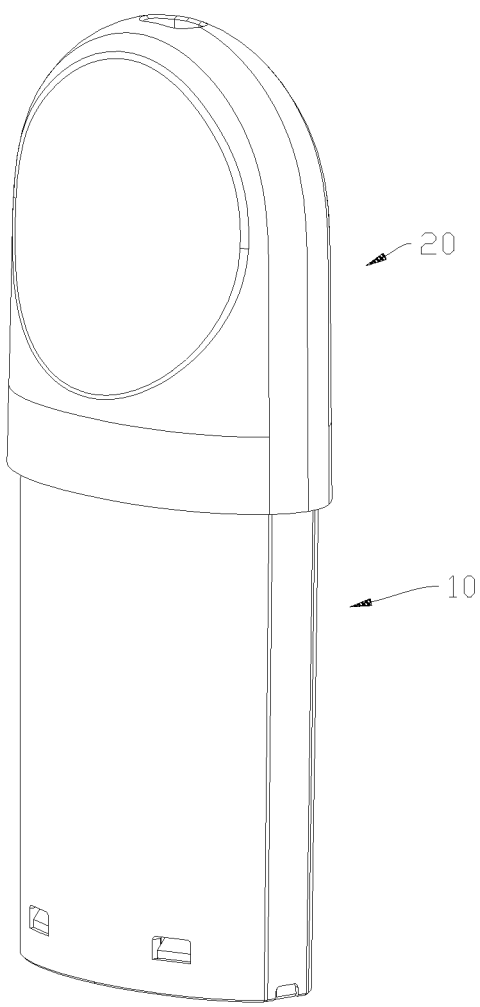
FIG. 4 is a schematic perspective view of an atomizer of the electronic atomization device shown in FIG. 1.
Figure 5:
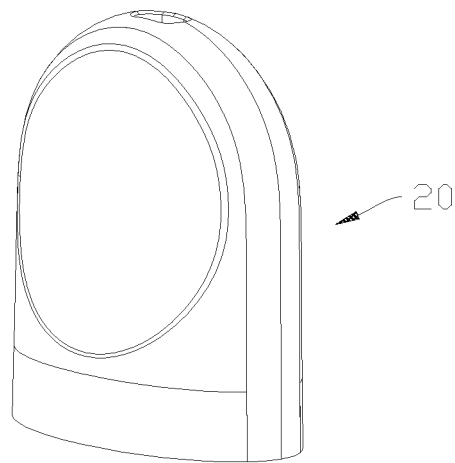
FIG. 5 is a partially exploded schematic view of the atomizer shown in FIG. 4.
Figure 5:
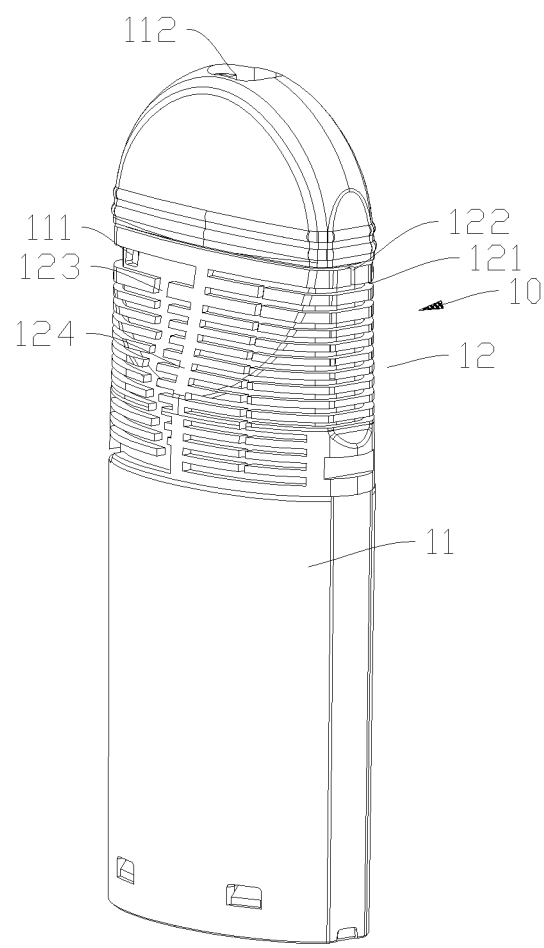
Figure 6:
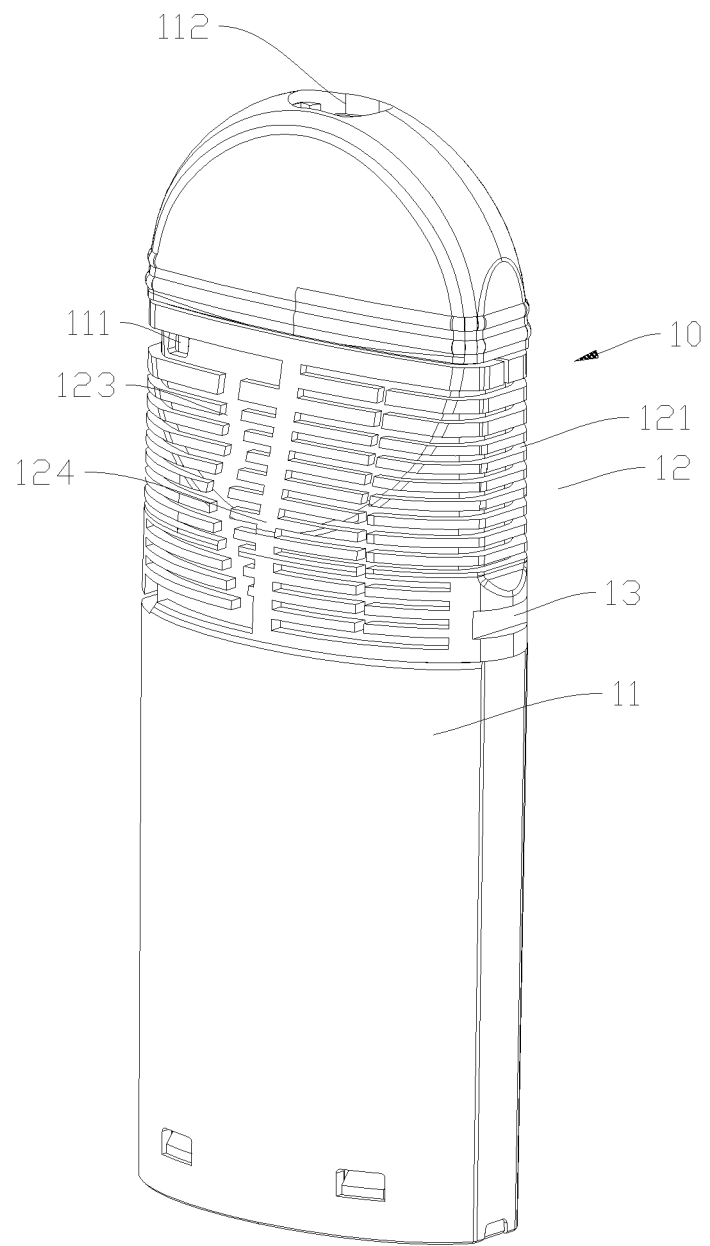
FIG. 6 is a schematic perspective view of a housing of the atomizer shown in FIG. 4.

FIGS. 1 to 3 show an electronic atomization device according to some embodiments of the present disclosure, which may be applied to atomize liquid media such as cigarette liquid or medicine liquid and may include an atomizer 1 and a power supply device 2 connected to the atomizer 1 mechanically and electrically.

As shown in FIGS. 4 to 7, the atomizer 1 includes a housing 10 for receiving an atomization medium and an atomization assembly, and an inhalation mouthpiece 20 sleeved outside an upper portion of the housing 10 to facilitate a user to inhale atomized vapour.

As shown in FIGS. 5-9, in some embodiments, the housing 10 includes a housing body 11 having an interior hollow structure. The housing 10 is provided with a second air inlet port 111, which may be located at an upper portion of the housing body 11. The housing body 11 is further provided with an air outlet port 112, which is located at a top of the housing body 11. A first partition wall 113 and a second partition wall 114 may be provided inside the housing body 11, with the first partition wall 113 and the second partition wall 114 spaced apart from each other, the first partition wall 113 spaced from an inner sidewall on one side of the housing body 11 by a first interval, and the second partition wall 114 spaced from an inner sidewall on the other side of the housing body 11 by a second interval. A second air inlet channel 115 and a second air outlet channel 116 are provided inside the housing 10. Specifically, the second air inlet channel 115 may be formed by the first interval, and the second air outlet channel 116 may be formed by the second interval. The space between the first partition wall 113 and the second partition wall 114 forms a liquid storage cavity 117.

In some embodiments, a liquid absorption structure 12 is further provided on an outer sidewall of the housing 10, at the upper portion and on an outer sidewall of the housing body 11. The liquid absorption structure 12 includes a plurality of first liquid absorption microgrooves 121. The plurality of first liquid absorption microgrooves 121 are arranged side by side in a longitudinal direction of the housing body 11, and each first liquid absorption microgroove 121 is arranged to extend along a circumferential direction of the housing 10. The first liquid absorption microgroove 121 has a groove width of 0.05-1 mm. For example, the groove width of the first liquid absorption microgroove 121 is 0.25 mm. When the condensate in the second air inlet channel 115 flows out from the second air inlet port 111, the first liquid absorption microgroove 121 can absorb most of the condensate by capillary tension to prevent it from flowing to the outer sidewall of the housing 10 and the outside of the atomizer, thereby improving the user experience and the aesthetic appearance effect of the atomizer.

In some embodiments, the plurality of first liquid absorption microgrooves 121 may be located below the second air inlet port 111, and one of the plurality of first liquid absorption microgrooves 121 close to the second air inlet port 111 communicates with the first air outlet channel 116, so as to absorb the condensate in the first air outlet channel 116 into the first liquid absorption microgrooves 121 and store the condensate leaked from the first air outlet channel 116. It should be understood that in some other embodiments, any one or more of the plurality of first liquid absorption microgrooves 121, not limited to the one close to the second air inlet port 111, may be communicated with the first air outlet channel 116. In some embodiments, the upper portion of the housing 10 may be provided with a liquid guiding groove 122. The liquid guiding groove 122 is arranged to extend along the longitudinal direction of the housing body 11, and is communicated with the first liquid absorption microgroove 121 and with the first air outlet channel 116. Specifically, the liquid guiding groove 122 is communicated with the first liquid absorption microgroove 121 close to the second air inlet port 111 and with the first air outlet channel 116, for guiding the condensate from the first air outlet channel 116 into that first liquid absorption microgroove 121. The liquid guiding groove 122 has a groove width less than or equal to that of the first liquid absorption microgroove 121, and provides capillary force to absorb the condensate from the first air outlet channel 116.

Further, in some embodiments, the upper portion of the housing 10 is further provided with a plurality of air inlet grooves 123. The air inlet grooves 123 are spaced at intervals along the circumference direction of the housing 10. It should be understood that in some other embodiments, there may be only one air inlet groove 123 instead of providing the plurality of the air inlet grooves 123. The plurality of air inlet grooves 123 may be arranged on the outer sidewall of the housing body 11, such that each air inlet groove 123 is in communication with the second air inlet port 111 and the outside, so as to allow outside air to enter the second air inlet channel 115 via the second air inlet port 111. Each air inlet groove 123 longitudinally traverses each first liquid absorption microgroove 122. In some embodiments, some of the plurality of air inlet grooves 123 are arranged to extend along the longitudinal direction of the housing 10, and some of the air inlet grooves 123 are configured to have a bent form. The bent form of the air inlet groove 123 may further obstruct the flow of condensate, so that the condensate flowing into the air inlet groove 123 can be more easily absorbed by the adjacent first liquid absorption microgroove 122. It should be understood that in some embodiments, instead of being arranged in the bent form, the first liquid absorption microgrooves 122 may be arranged in a spiral form or all of them may be arranged to extend along the longitudinal direction.

Further, in some embodiments, two opposite outer sidewalls of the housing 10 are further provided with partition walls 124. The partition walls 124 may be arranged on the upper portion of the housing body 11, and may extend along the longitudinal direction of the housing body 11 and traverse each first liquid-absorption microgroove 121 to partition the first liquid-absorption microgroove 121.

Figure 9:
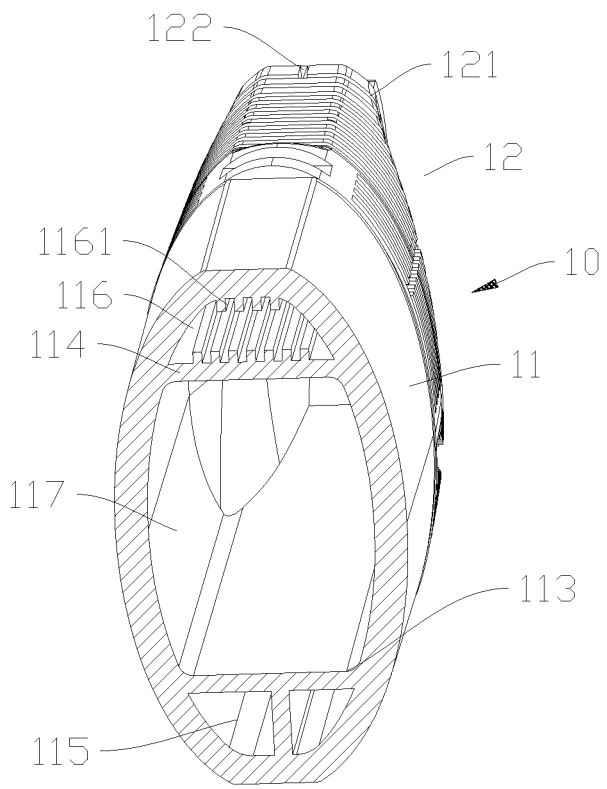
FIG. 9 is a transverse sectional view of a housing of the atomizer shown in FIG. 8.

Referring to FIG. 9, in some embodiments, the inner sidewall of the first air outlet channel 116 is provided with a plurality of second liquid absorption microgrooves 1161. The second liquid absorption microgrooves 1161 may be provided on two opposite inner sidewalls of the first air outlet channel 116, and may be spaced apart from each other. It should be understood that in some other embodiments, there may be only one second liquid absorption microgroove 1161 instead of providing the plurality of the second liquid absorption microgrooves 1161. The second liquid absorption microgroove 1161 may be arranged to extend along a longitudinal direction of the first air outlet channel 116, with one end thereof extending toward a top wall of the housing 10. It should be understood that in some other embodiments, the second liquid-absorption microgroove 1161 may be arranged to extend spirally instead of being arranged to extend longitudinally. In some embodiments, the second liquid absorption microgroove 1161 has a depth that may be gradually reduced toward the end away from the air outlet port 112, and thus the second liquid absorption microgroove 1161 has an inclined bottom surface extending toward the air outlet port 112. As a result, the second liquid absorption microgroove 1161 has a less liquid storage at its upper portion than a liquid storage at its lower portion, thereby preventing the liquid in the second liquid absorption microgroove 1161 from being inhaled into the mouth by the user. In some embodiments, the second liquid absorption microgroove 1161 may have a groove width that is gradually increased towards the air outlet port 112, such that the second liquid absorption microgroove 1161 may have a narrow inside and a wide opening, thereby facilitating the flowing of the liquid to the atomization assembly 50 along the second liquid absorption microgroove 1161. In some embodiments, the groove width of the second liquid absorption microgroove 1161 may be 0.05-1 mm.

Further, in some embodiments, the inhalation mouthpiece 20 includes a main body 21 that is sleeved on the upper portion of the housing 10. The inhalation mouthpiece 20 and the housing 10 define a first air inlet channel 22 therebetween. The first air inlet channel 22 is formed by the space provided between the inhalation mouthpiece 20 and the housing 10. The first air inlet channel 22 is in communication with the outside environment. The liquid absorption structure 12 is located in the first air inlet channel 22. The plurality of first liquid absorption microgrooves 121 and the air inlet grooves 123 are arranged on an outer sidewall portion of the housing 10 that is located within the first air inlet channel 22. In some embodiments, a first air inlet port 23 is provided between the open end of the inhalation mouthpiece 20 and the housing 10. The first air inlet port 23 is located at a lower end of the inhalation mouthpiece 20 that contacts with the housing 10. The first air inlet port 23 communicates with the first air inlet channel 22, and communicates with the air inlet groove 123. Air may enter the first air inlet channel 22 from the first air inlet port 23, and enter the second air inlet channel 115 directly from the second air inlet port 111, or air may alternatively enter the air inlet groove 123 from the first gas inlet port 23 and then enter the second air inlet channel 115 from the second air inlet port 111.

Further, in some embodiments, the inhalation mouthpiece 20 snaps with the housing 10. Specifically, in some embodiments, the outer sidewall of the housing 10 may be provided with snapping grooves 13, and the snapping grooves 13 are provided on two opposite sidewalls of the housing 10 below the first liquid absorption microgrooves 121. The inhalation mouthpiece 20 is provided with snapping ribs 24 close to its open end, and the snapping ribs 24 are located on two opposite inner sidewalls of the inhalation mouthpiece 20 corresponding to the snapping grooves 13. When the inhalation mouthpiece 20 being sleeved on the housing 10, the snapping ribs 24 are snapped into the snapping grooves 13 to fixedly connect the inhalation mouthpiece 20 with the housing 10.

Figure 7:
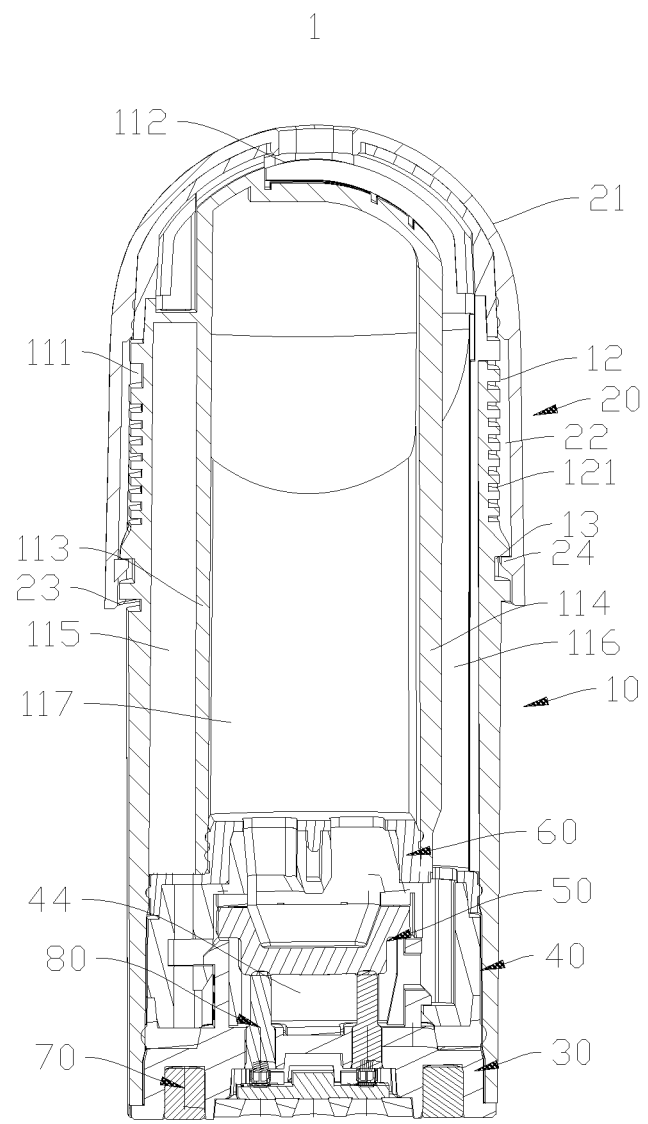
FIG. 7 is a cross-sectional view of the atomizer shown in FIG. 4.
Figure 8:
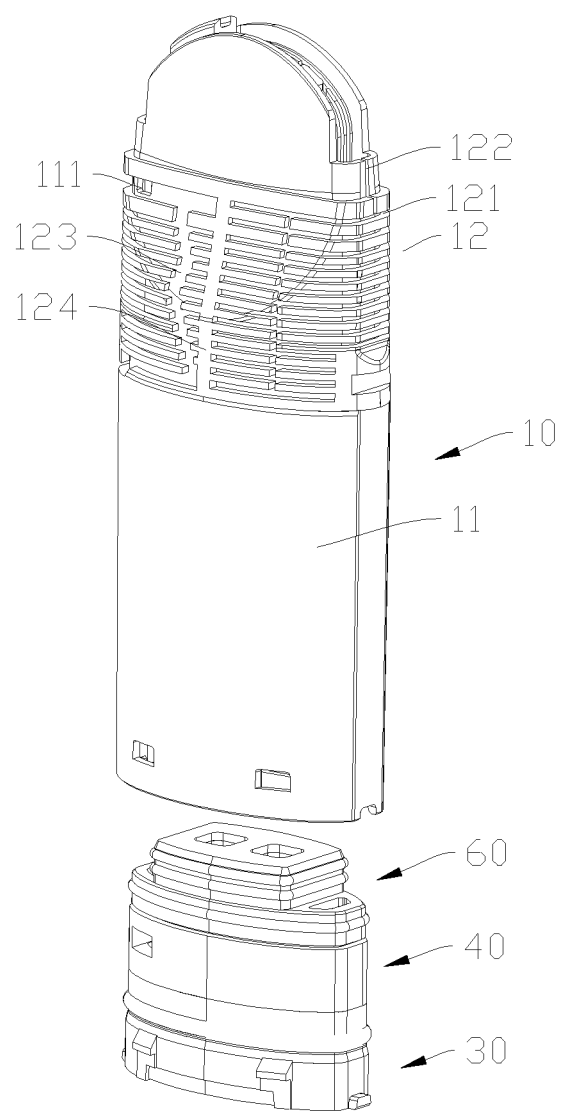
FIG. 8 is a partially exploded schematic view of the atomizer shown in FIG. 6.
Figure 10:
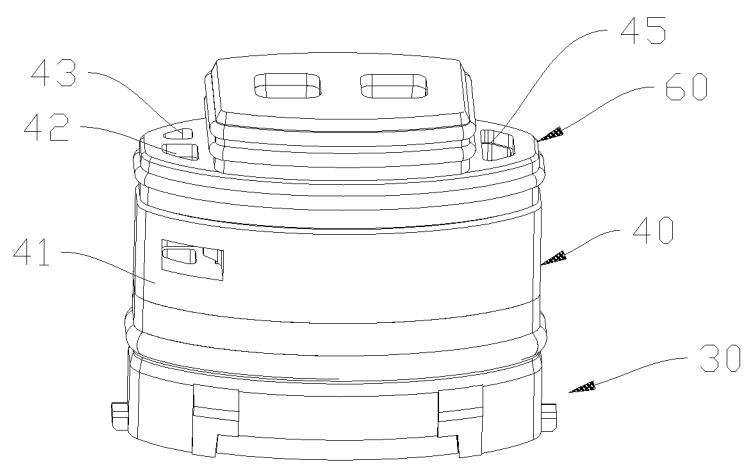
FIG. 10 is an assembled view the atomizer base and atomizer seat shown in FIG. 8.

As shown in FIG. 7, FIG. 8, and FIG. 10, in some embodiments, the atomizer further includes a base 30. The base 30 is provided at the open end of the housing 10, and the housing 10 is sleeved outside the base 30. The base 30 may be used for installing the atomization assembly 50 and the atomization seat 40.

In some embodiments, the atomizer further includes an atomization seat 40. The atomization seat 40 may be sleeved on the base 30. An atomization cavity 44 is provided inside the housing 10. Specifically, in some embodiments, the atomization seat 40 includes a cylindrical body 41 which has a hollow structure for forming the atomization cavity 44, and the second air inlet channel 115 and the first air outlet channel 116 both communicate with the atomization cavity 44. The atomization seat 40 is provided with a third air inlet channel 42 and an activation air channel 43. The third air inlet channel 42 is in communication with the second air inlet channel 115 and the atomization cavity 44, such that air in the third air inlet channel 42 may enter the atomization cavity 44. The activation air channel 43 and the third air inlet channel 42 are arranged side by side and in parallel, and the activation air channel 43 communicates with the second air inlet channel 115 and the power supply device 2, thereby allowing air to enter the power supply device 2. The atomization seat 40 is further provided with a second air outlet channel 45. The second air outlet channel 45 and the third air inlet channel 42 are respectively located on two opposite sides of the atomization cavity 44, and the second air outlet channel 45 communicates with the atomization cavity 44 and the first air outlet channel 116, thereby allowing the atomized vapour in the atomization cavity 44 to enter the second air outlet channel 116.

In some embodiments, the atomizer further includes an atomization assembly 50. The atomization assembly 50 may be arranged in the atomization seat 40 above the base 30. The atomization assembly 50 includes a porous body and a heating body arranged on the porous body. The porous body is arranged on the base 30 and communicates with the liquid storage cavity 117. For example, the porous body may be a ceramic porous body. In some embodiments, the heating body and the porous body may be sintered to form an integral structure, and the heating body may be used to heat and atomize atomization medium arranged in the porous body.

In some embodiments, the atomizer further includes a sealing structure 60. The sealing structure 60 is sleeved on an upper portion of the atomization seat 40 and located at a junction of the atomization seat 40 and the liquid storage cavity 117, and may be used to seal a gap between the atomization seat 40 and the housing 10. For example, the sealing structure 60 may be a silicone sleeve or a rubber sleeve. It should be understood that in some other embodiments, it may not be limited to the silicone sleeve or the rubber sleeve.

In some embodiments, the atomizer further includes a magnetic member 70. There may be two magnetic members 70, which are arranged on the base 30 at an interval and may be sucked with the power supply device 2. For example, the magnetic member 70 may be a magnet column.

In some embodiments, the atomizer further includes an electrode 80. There may be two electrode columns, i.e., a positive electrode column and a negative electrode column, which may be arranged side by side on the base 30, with one end conductively connected with the heating element, and the other end conductively connected with the power supply device.

As shown in FIGS. 1 to 3, in some embodiments, the power supply device 2 includes a power supply housing 201, a battery assembly 202 arranged in the power supply housing 201, and an ECM (Electret Condenser Microphone) switch 203 arranged in the power supply housing 201. The power supply housing 201 is sleeved on a portion of the atomizer 1, for housing the battery assembly 202, the ECM switch 203 and other components. The battery assembly 202 is conductively connected to the electrode 80 and the ECM switch 203. Specifically, the battery assembly 202 provides a conductive column for abutting against the electrode 80. The ECM switch 203 communicates with the activation air channel 43 so as to activate the battery assembly 202 for powering the atomization assembly 50. The power supply housing 20 is further provided with an isolation sleeve 204. The isolation sleeve 204 is arranged at a junction of the power supply housing 20 and the atomizer and may isolate the atomizer 1 from the battery assembly 202 and other components. The conductive column 202 is arranged on the isolation sleeve 204. The isolation sleeve 204 is further provided with a magnetic fixing member 204 that is arranged corresponding to the magnetic member 70 and used to fix the isolation sleeve 204 by means of magnetic attraction between the magnetic fixing member 204 and the magnetic member 70.

Although aspects of the disclosure have been described in detail with reference to certain preferred constructions, variations and modifications exist within the scope and spirit of one or more independent aspects of the disclosure as described. One or more independent features and/or independent advantages of the disclosure may be set forth in the following claims:

What is claimed is:

1. An atomizer comprising a housing (10) and an inhalation mouthpiece (20) sleeved on an upper portion of the housing (10), wherein the inhalation mouthpiece (20) and the housing (10) define therebetween a first air inlet channel (22) communicating with an outside environment;
    wherein the housing (10) is provided with a second air inlet port (111) communicating with the first air inlet channel (22); and
    wherein the first air inlet channel (22) is provided with a liquid absorption structure (12), which comprises a plurality of first liquid absorption microgrooves (121) provided on an outer sidewall portion of the housing (10) that is located within the first air inlet channel (22).

2. The atomizer according to claim 1, wherein each of the first liquid absorption microgrooves (121) is arranged to extend along a circumference direction of the housing (10).

3. The atomizer according to claim 1, wherein the first liquid absorption microgroove (121) has a groove width of 0.05-1 mm.

4. The atomizer according to claim 1, wherein at least one air inlet groove (123) is formed on the outer sidewall portion of the housing (10) that is located within the first air inlet channel (22), and the air inlet groove (123) communicating with the first air inlet channel (22) and the second air inlet port (111).

5. The atomizer according to claim 4, wherein the at least one air inlet groove (123) traverses the first liquid absorption microgroove (121).

6. The atomizer according to claim 4, wherein the air inlet groove (123) is arranged to extend along a longitudinal direction of the housing (10).

7. The atomizer according to claim 4, wherein the air inlet groove (123) is arranged in a bent or spiral form.

8. The atomizer according to claim 4, wherein a first air inlet port communicating with the first air inlet channel (22) is provided between an open end portion of the inhalation mouthpiece (20) and the housing (10), and the air inlet groove (123) communicates with the first air inlet port (23).

9. The atomizer according to claim 1, wherein an atomization cavity (44) is provided inside the housing (10); and
    wherein a second air inlet channel (115) and a first air outlet channel (116) that are in communication with the atomization cavity (44) are formed inside the housing (10), and the second air inlet channel (115) communicates with the second air inlet portion (111).

10. The atomizer according to claim 9, wherein at least one of the plurality of first liquid absorption microgrooves (121) communicates with the air outlet channel (116).

11. The atomizer according to claim 10, wherein a liquid guiding groove (122) communicating the first liquid absorption microgroove (121) with the first air outlet channel (116) is formed on the outer sidewall of the upper portion of the housing (10).

12. The atomizer according to claim 10, further comprising an atomization seat (40) arranged in the housing (10), and an atomization assembly (50) arranged in the atomization seat (40);
    wherein the atomization cavity (44) is formed inside the atomization seat (40); and
    wherein the atomization seat (40) is provided with a third air inlet channel (42) communicating with the second air inlet channel (115) and the atomization cavity (44), an activation air channel (43) communicating with the second air inlet channel (115), and a second air outlet channel (45) communicating with the atomization cavity (44) and the first air outlet channel (116).

13. The atomizer according to claim 12, wherein the activation air channel (43) and the third air inlet channel (42) are arranged side by side and in parallel.

14. An electronic atomization device, comprising a power supply device and an atomizer connected to the power supply device, the atomizer comprising a housing (10) and an inhalation mouthpiece (20) sleeved on an upper portion of the housing (10), wherein the inhalation mouthpiece (20) and the housing (10) define therebetween a first air inlet channel (22) communicating with an outside environment;
    wherein the housing (10) is provided with a second air inlet port (111) communicating with the first air inlet channel (22); and
    wherein the first air inlet channel (22) is provided with a liquid absorption structure (12), which comprises a plurality of first liquid absorption microgrooves (121) provided on an outer sidewall portion of the housing (10) that is located within the first air inlet channel (22).

15. The electronic atomization device according to claim 14, wherein each of the first liquid absorption microgrooves (121) is arranged to extend along a circumference direction of the housing (10).

16. The electronic atomization device according to claim 14, wherein the first liquid absorption microgroove (121) has a groove width of 0.05-1 mm.

17. The electronic atomization device according to claim 14, wherein at least one air inlet groove (123) is formed on the outer sidewall portion of the housing (10) that is located within the first air inlet channel (22), and the air inlet groove (123) communicating with the first air inlet channel (22) and the second air inlet port (111).

18. The electronic atomization device according to claim 17, wherein the air inlet groove (123) is arranged in a bent or spiral form.

19. The electronic atomization device according to claim 14, wherein an atomization cavity (44) is provided inside the housing (10);
    wherein a second air inlet channel (115) and a first air outlet channel (116) that are in communication with the atomization cavity (44) are formed inside the housing (10), and the second air inlet channel (115) communicates with the second air inlet portion (111); and
    wherein at least one of the plurality of first liquid absorption microgrooves (121) communicates with the air outlet channel (116).

20. The electronic atomization device according to claim 19, wherein a liquid guiding groove (122) communicating the first liquid absorption microgroove (121) with the first air outlet channel (116) is formed on the outer sidewall of the upper portion of the housing (10).

* * * * *